US008684902B2

(12) United States Patent
Wampler et al.

(10) Patent No.: US 8,684,902 B2
(45) Date of Patent: Apr. 1, 2014

(54) ROTARY BLOOD PUMP

(75) Inventors: Richard K. Wampler, Loomis, CA (US); David M. Lancisi, Folsom, CA (US)

(73) Assignee: Thoratec Corporation, Pleasanton, CA (US)

( * ) Notice: Subject to any disclaimer, the term of this patent is extended or adjusted under 35 U.S.C. 154(b) by 1502 days.

(21) Appl. No.: 11/950,318

(22) Filed: Dec. 4, 2007

(65) Prior Publication Data

US 2008/0095648 A1 Apr. 24, 2008

Related U.S. Application Data

(62) Division of application No. 10/940,419, filed on Sep. 14, 2004, now Pat. No. 7,431,688.

(60) Provisional application No. 60/504,233, filed on Sep. 18, 2003.

(51) Int. Cl.
*A61M 1/10* (2006.01)

(52) U.S. Cl.
USPC ............................................ 600/16; 417/420

(58) Field of Classification Search
USPC .................. 417/352, 356, 410.5, 420, 423.1, 417/423.12, 423.7, 424.2; 600/16, 17; 604/151
See application file for complete search history.

(56) References Cited

U.S. PATENT DOCUMENTS

| 1,902,418 | A | 3/1933 | Pilgrim |
| 2,356,659 | A | 8/1944 | Aguiar |
| 2,649,052 | A | 8/1953 | Weyer |
| 2,664,050 | A | 12/1953 | Abresch |
| 2,684,035 | A | 7/1954 | Kemp |
| 2,789,511 | A | 4/1957 | Dobie |
| 2,935,068 | A | 5/1960 | Donaldson |
| 3,080,824 | A | 3/1963 | Boyd et al. |
| 3,420,184 | A | 1/1969 | Englesberg et al. |
| 3,510,229 | A | 5/1970 | Smith |

(Continued)

FOREIGN PATENT DOCUMENTS

| CA | 2 264 538 A1 | 2/1998 |
| CA | 2 407 938 A1 | 11/2001 |

(Continued)

OTHER PUBLICATIONS

G.H. Jang, et al., "Nonlinear Dynamic Analysis of a Hydrodynamic Journal Bearing Considering the Effect of a Rotating or Stationary Herringbone Groove," *ASME Journal of Tribology*, STLE/ASME Tribology Conference, San Francisco, California, Oct. 22-24, 2001, pp. 297-304.

(Continued)

*Primary Examiner* — Christopher D Koharski
*Assistant Examiner* — Frances Oropeza
(74) *Attorney, Agent, or Firm* — Inskeep IP Group, Inc.

(57) ABSTRACT

Various "contactless" bearing mechanisms including hydrodynamic and magnetic bearings are provided for a rotary pump as alternatives to mechanical contact bearings. In one embodiment, a pump apparatus includes a pump housing defining a pumping chamber. The housing has a spindle extending into the pumping chamber. A spindle magnet assembly includes first and second magnets disposed within the spindle. The first and second magnets are arranged proximate each other with their respective magnetic vectors opposing each other. The lack of mechanical contact bearings enables longer life pump operation and less damage to working fluids such as blood.

39 Claims, 5 Drawing Sheets

(56) References Cited

U.S. PATENT DOCUMENTS

| | | | |
|---|---|---|---|
| 3,608,088 A | 9/1971 | Dorman et al. | |
| 3,647,324 A | 3/1972 | Rafferty et al. | |
| 3,753,623 A | 8/1973 | Wutz | |
| 3,812,812 A | 5/1974 | Hurwitz | |
| 3,860,968 A | 1/1975 | Shapiro | |
| 3,960,468 A | 6/1976 | Boorse et al. | |
| 4,082,376 A | 4/1978 | Wehde et al. | |
| 4,135,253 A | 1/1979 | Reich et al. | |
| 4,149,535 A | 4/1979 | Volder | |
| 4,304,524 A | 12/1981 | Coxon | |
| 4,382,199 A | 5/1983 | Isaacson | |
| 4,392,836 A | 7/1983 | Sugawara | |
| 4,458,366 A | 7/1984 | MacGregor | |
| 4,540,402 A | 9/1985 | Aigner | |
| 4,589,822 A | 5/1986 | Clausen et al. | |
| 4,625,712 A | 12/1986 | Wampler | |
| 4,645,433 A | 2/1987 | Hauenstein | |
| 4,686,982 A | 8/1987 | Nash | |
| 4,688,998 A | 8/1987 | Olsen et al. | |
| 4,704,121 A | 11/1987 | Moise | |
| 4,753,221 A | 6/1988 | Kensey et al. | |
| 4,769,006 A | 9/1988 | Papantonakos | |
| 4,779,614 A | 10/1988 | Moise | |
| 4,806,080 A * | 2/1989 | Mizobuchi et al. | 417/353 |
| 4,812,108 A | 3/1989 | Kotera | |
| 4,817,586 A | 4/1989 | Wampler | |
| 4,846,152 A | 7/1989 | Wampler et al. | |
| 4,895,557 A | 1/1990 | Moise et al. | |
| 4,900,227 A | 2/1990 | Trouplin | |
| 4,902,272 A | 2/1990 | Milder et al. | |
| 4,906,229 A | 3/1990 | Wampler | |
| 4,908,012 A | 3/1990 | Moise et al. | |
| 4,919,647 A | 4/1990 | Nash | |
| 4,930,997 A | 6/1990 | Bennett | |
| 4,944,722 A | 7/1990 | Carriker et al. | |
| 4,944,748 A | 7/1990 | Bramm et al. | |
| 4,957,504 A | 9/1990 | Chardack | |
| 4,964,864 A | 10/1990 | Summers et al. | |
| 4,969,865 A | 11/1990 | Hwang et al. | |
| 4,984,972 A | 1/1991 | Clausen et al. | |
| 4,985,014 A | 1/1991 | Orejola | |
| 4,994,017 A | 2/1991 | Yozu | |
| 4,994,722 A | 2/1991 | Dolan et al. | |
| 4,995,857 A | 2/1991 | Arnold | |
| 5,021,048 A | 6/1991 | Buckholtz | |
| 5,036,235 A | 7/1991 | Kleckner | |
| 5,049,134 A | 9/1991 | Golding et al. | |
| 5,055,005 A | 10/1991 | Kletschka | |
| 5,089,016 A | 2/1992 | Millner et al. | |
| 5,092,844 A | 3/1992 | Schwartz et al. | |
| 5,098,256 A | 3/1992 | Smith | |
| 5,106,273 A | 4/1992 | Lemarquand et al. | |
| 5,106,372 A | 4/1992 | Ranford | |
| 5,112,200 A | 5/1992 | Isaacson et al. | |
| 5,112,202 A | 5/1992 | Oshima et al. | |
| 5,112,349 A | 5/1992 | Summers et al. | |
| 5,129,883 A | 7/1992 | Black | |
| 5,147,186 A | 9/1992 | Buckholtz | |
| 5,171,212 A | 12/1992 | Buck et al. | |
| 5,190,528 A | 3/1993 | Fonger et al. | |
| 5,195,877 A | 3/1993 | Kletschka | |
| 5,201,679 A | 4/1993 | Velte et al. | |
| 5,209,650 A | 5/1993 | Lemieux | |
| 5,211,546 A | 5/1993 | Isaacson et al. | |
| 5,290,227 A | 3/1994 | Pasque | |
| 5,300,112 A | 4/1994 | Barr | |
| 5,312,341 A | 5/1994 | Turi | |
| 5,324,177 A | 6/1994 | Golding et al. | |
| 5,346,458 A | 9/1994 | Affeld | |
| 5,360,317 A | 11/1994 | Clausen et al. | |
| 5,360,445 A | 11/1994 | Goldowsky | |
| 5,370,509 A | 12/1994 | Golding et al. | |
| 5,376,114 A | 12/1994 | Jarvik | |
| 5,385,581 A | 1/1995 | Bramm et al. | |
| 5,405,383 A | 4/1995 | Barr | |
| 5,437,541 A | 8/1995 | Vainrub | |
| 5,449,342 A | 9/1995 | Hirose et al. | |
| 5,451,147 A | 9/1995 | Sakagami et al. | |
| 5,458,459 A | 10/1995 | Hubbard et al. | |
| 5,470,208 A | 11/1995 | Kletschka | |
| 5,505,701 A | 4/1996 | Anaya Fernandez de Lomana | |
| 5,527,159 A | 6/1996 | Bozeman, Jr. et al. | |
| 5,533,957 A | 7/1996 | Aldea | |
| 5,588,812 A | 12/1996 | Taylor et al. | |
| 5,595,762 A | 1/1997 | Derrieu et al. | |
| 5,613,935 A | 3/1997 | Jarvik | |
| 5,643,226 A | 7/1997 | Cosgrove et al. | |
| 5,678,306 A | 10/1997 | Bozeman, Jr. et al. | |
| 5,685,700 A | 11/1997 | Israelev | |
| 5,695,471 A * | 12/1997 | Wampler | 604/131 |
| 5,707,218 A | 1/1998 | Maher et al. | |
| 5,713,730 A | 2/1998 | Nosé et al. | |
| 5,722,930 A | 3/1998 | Larson, Jr. et al. | |
| 5,738,649 A | 4/1998 | Macoviak | |
| 5,746,575 A | 5/1998 | Westphal et al. | |
| 5,746,709 A | 5/1998 | Rom et al. | |
| 5,749,855 A | 5/1998 | Reitan | |
| 5,755,784 A | 5/1998 | Jarvik | |
| 5,776,111 A | 7/1998 | Tesio | |
| 5,807,311 A | 9/1998 | Palestrant | |
| 5,814,011 A | 9/1998 | Corace | |
| 5,824,070 A | 10/1998 | Jarvik | |
| 5,840,070 A | 11/1998 | Wampler | |
| 5,851,174 A | 12/1998 | Jarvik et al. | |
| 5,853,394 A | 12/1998 | Tolkoff et al. | |
| 5,868,702 A | 2/1999 | Stevens et al. | |
| 5,868,703 A | 2/1999 | Bertolero et al. | |
| 5,888,242 A | 3/1999 | Antaki et al. | |
| 5,890,883 A | 4/1999 | Golding et al. | |
| 5,911,685 A | 6/1999 | Siess et al. | |
| 5,921,913 A | 7/1999 | Siess | |
| 5,938,412 A | 8/1999 | Israelev | |
| 5,941,813 A | 8/1999 | Sievers et al. | |
| 5,947,703 A | 9/1999 | Nojiri et al. | |
| 5,951,263 A | 9/1999 | Taylor et al. | |
| 5,964,694 A | 10/1999 | Siess et al. | |
| 6,004,269 A | 12/1999 | Crowley et al. | |
| 6,007,479 A | 12/1999 | Rottenberg et al. | |
| 6,058,593 A | 5/2000 | Siess | |
| 6,071,093 A * | 6/2000 | Hart | 417/424.2 |
| 6,074,436 A | 6/2000 | Wang et al. | |
| 6,080,133 A | 6/2000 | Wampler | |
| 6,083,260 A | 7/2000 | Aboul-Hosn | |
| 6,086,527 A | 7/2000 | Talpade | |
| 6,123,659 A | 9/2000 | le Blanc et al. | |
| 6,123,726 A | 9/2000 | Mori et al. | |
| 6,132,363 A | 10/2000 | Freed et al. | |
| 6,135,943 A | 10/2000 | Yu et al. | |
| 6,139,487 A | 10/2000 | Siess | |
| 6,155,969 A | 12/2000 | Schima et al. | |
| 6,176,822 B1 | 1/2001 | Nix et al. | |
| 6,176,848 B1 | 1/2001 | Rau et al. | |
| 6,190,304 B1 | 2/2001 | Downey et al. | |
| 6,200,260 B1 | 3/2001 | Bolling | |
| 6,227,797 B1 | 5/2001 | Watterson et al. | |
| 6,227,817 B1 | 5/2001 | Paden | |
| 6,227,820 B1 | 5/2001 | Jarvik | |
| 6,234,772 B1 | 5/2001 | Wampler et al. | |
| 6,234,998 B1 | 5/2001 | Wampler | |
| 6,244,835 B1 | 6/2001 | Antaki et al. | |
| 6,245,007 B1 | 6/2001 | Bedingham et al. | |
| 6,247,892 B1 | 6/2001 | Kazatchkov et al. | |
| 6,250,880 B1 | 6/2001 | Woodard et al. | |
| 6,254,359 B1 | 7/2001 | Aber | |
| 6,264,635 B1 | 7/2001 | Wampler et al. | |
| 6,293,901 B1 | 9/2001 | Prem | |
| 6,295,877 B1 | 10/2001 | Aboul-Hosn et al. | |
| 6,368,083 B1 | 4/2002 | Wampler | |
| 6,387,037 B1 | 5/2002 | Bolling et al. | |
| 6,394,769 B1 | 5/2002 | Bearnson et al. | |
| 6,422,990 B1 | 7/2002 | Prem | |
| 6,425,007 B1 | 7/2002 | Messinger | |
| 6,428,464 B1 | 8/2002 | Bolling | |
| 6,447,266 B2 | 9/2002 | Antaki et al. | |

(56) References Cited

U.S. PATENT DOCUMENTS

| | | |
|---|---|---|
| 6,447,441 B1 | 9/2002 | Yu et al. |
| 6,508,777 B1 | 1/2003 | Macoviak et al. |
| 6,508,787 B2 | 1/2003 | Erbel et al. |
| 6,517,315 B2 | 2/2003 | Belady |
| 6,532,964 B2 | 3/2003 | Aboul-Hosn et al. |
| 6,533,716 B1 | 3/2003 | Schmitz-Rode et al. |
| 6,537,315 B2 | 3/2003 | Yamazaki et al. |
| 6,544,216 B1 | 4/2003 | Sammler et al. |
| 6,547,519 B2 | 4/2003 | deBlanc et al. |
| 6,595,762 B2 | 7/2003 | Khanwilkar et al. |
| 6,609,883 B2 | 8/2003 | Woodard et al. |
| 6,610,004 B2 | 8/2003 | Viole et al. |
| 6,623,420 B2 | 9/2003 | Reich et al. |
| 6,638,011 B2 | 10/2003 | Woodard et al. |
| 6,641,378 B2 * | 11/2003 | Davis et al. ............... 417/423.7 |
| 6,641,558 B1 | 11/2003 | Aboul-Hosn et al. |
| 6,688,861 B2 | 2/2004 | Wampler |
| 6,692,318 B2 | 2/2004 | McBride |
| 6,709,418 B1 | 3/2004 | Aboul-Hosn et al. |
| 6,716,189 B1 | 4/2004 | Jarvik et al. |
| 6,749,598 B1 | 6/2004 | Keren et al. |
| 6,776,578 B2 | 8/2004 | Belady |
| 6,783,328 B2 | 8/2004 | Lucke et al. |
| 6,790,171 B1 | 9/2004 | Gründeman et al. |
| 6,794,789 B2 | 9/2004 | Siess et al. |
| 6,808,371 B2 * | 10/2004 | Niwatsukino et al. ........ 417/353 |
| 6,817,836 B2 | 11/2004 | Nose et al. |
| 6,860,713 B2 | 3/2005 | Hoover |
| 6,866,625 B1 | 3/2005 | Ayre et al. |
| 6,926,662 B1 | 8/2005 | Aboul-Hosn et al. |
| 6,935,344 B1 | 8/2005 | Aboul-Hosn et al. |
| 6,942,611 B2 | 9/2005 | Siess |
| 6,949,066 B2 | 9/2005 | Bearnson et al. |
| 6,966,748 B2 | 11/2005 | Woodard et al. |
| 6,974,436 B1 | 12/2005 | Aboul-Hosn et al. |
| 6,981,942 B2 | 1/2006 | Khaw et al. |
| 6,984,392 B2 | 1/2006 | Bechert et al. |
| 7,010,954 B2 | 3/2006 | Siess et al. |
| 7,011,620 B1 | 3/2006 | Siess |
| 7,022,100 B1 | 4/2006 | Aboul-Hosn et al. |
| 7,027,875 B2 | 4/2006 | Siess et al. |
| 7,070,055 B2 | 7/2006 | Lechanoine et al. |
| 7,074,016 B1 | 7/2006 | Epstein et al. |
| 7,122,019 B1 | 10/2006 | Kesten et al. |
| 7,150,711 B2 | 12/2006 | Nüsser et al. |
| 7,156,802 B2 | 1/2007 | Woodard et al. |
| 7,160,243 B2 | 1/2007 | Medvedev |
| 7,172,551 B2 | 2/2007 | Leasure |
| 7,175,588 B2 | 2/2007 | Morello |
| 7,241,257 B1 | 7/2007 | Ainsworth et al. |
| 7,284,956 B2 | 10/2007 | Nose et al. |
| 7,329,236 B2 | 2/2008 | Kesten et al. |
| 7,331,921 B2 | 2/2008 | Viole et al. |
| 7,335,192 B2 | 2/2008 | Keren et al. |
| 7,393,181 B2 | 7/2008 | McBride et al. |
| 7,476,077 B2 | 1/2009 | Woodard et al. |
| 7,491,163 B2 | 2/2009 | Viole et al. |
| 7,731,675 B2 | 6/2010 | Aboul-Hosn et al. |
| 7,841,976 B2 | 11/2010 | McBride et al. |
| 7,888,242 B2 | 2/2011 | Tanaka et al. |
| 2001/0031210 A1 | 10/2001 | Antaki et al. |
| 2002/0151761 A1 | 10/2002 | Viole et al. |
| 2002/0169413 A1 | 11/2002 | Keren et al. |
| 2003/0135086 A1 | 7/2003 | Khaw et al. |
| 2003/0208097 A1 | 11/2003 | Aboul-Hosn et al. |
| 2003/0231959 A1 | 12/2003 | Snider |
| 2004/0029842 A1 | 2/2004 | Gardner |
| 2004/0101406 A1 | 5/2004 | Hoover |
| 2004/0153104 A1 | 8/2004 | Buckman et al. |
| 2004/0236420 A1 | 11/2004 | Yamane et al. |
| 2005/0055038 A1 | 3/2005 | Kelleher et al. |
| 2005/0069426 A1 | 3/2005 | Mason et al. |
| 2005/0069435 A1 | 3/2005 | Ikeya et al. |
| 2005/0095124 A1 | 5/2005 | Arnold et al. |
| 2005/0095151 A1 | 5/2005 | Wampler et al. |
| 2005/0165269 A9 | 7/2005 | Aboul-Hosn et al. |
| 2006/0018943 A1 | 1/2006 | Bechert et al. |
| 2006/0058869 A1 | 3/2006 | Olson et al. |
| 2006/0226423 A1 | 10/2006 | Yamasaki |
| 2007/0100314 A1 | 5/2007 | Keren et al. |
| 2007/0203442 A1 | 8/2007 | Bechert et al. |
| 2008/0103442 A1 | 5/2008 | Kesten et al. |
| 2008/0103591 A1 | 5/2008 | Siess |
| 2008/0306327 A1 | 12/2008 | Shifflette |
| 2009/0023975 A1 | 1/2009 | Marseille et al. |
| 2009/0060743 A1 | 3/2009 | McBride et al. |
| 2009/0071137 A1 | 3/2009 | Harris |
| 2009/0093764 A1 | 4/2009 | Pfeffer et al. |
| 2009/0093765 A1 | 4/2009 | Glenn |
| 2009/0093796 A1 | 4/2009 | Pfeffer et al. |
| 2009/0171137 A1 | 7/2009 | Farnan et al. |
| 2009/0182188 A1 | 7/2009 | Marseille et al. |
| 2010/0087773 A1 | 4/2010 | Ferrari |
| 2010/0191035 A1 | 7/2010 | Kang et al. |
| 2011/0004046 A1 | 1/2011 | Campbell et al. |

FOREIGN PATENT DOCUMENTS

| | | |
|---|---|---|
| CA | 2 468 546 a1 | 11/2004 |
| DE | 42 40 718 A1 | 6/1993 |
| DE | 196 13 388 A1 | 10/1996 |
| EP | 0 364 293 A2 | 10/1989 |
| EP | 0 533 432 A1 | 9/1992 |
| EP | 0 810 374 A2 | 12/1997 |
| EP | 810374 A2 | 12/1997 |
| EP | 1 481 699 A1 | 12/2004 |
| EP | 1481699 A1 | 12/2004 |
| FR | 2267800 A1 | 4/1974 |
| JP | 48-23295 | 3/1973 |
| JP | 1-129898 A | 5/1989 |
| JP | 2002-093120 | 4/1990 |
| JP | 2004-236818 A | 8/1992 |
| JP | 2000-509311 A | 7/2000 |
| JP | 2002-130177 A | 5/2002 |
| JP | 2002-315824 A | 10/2002 |
| JP | 2003-503639 A | 1/2003 |
| JP | 2003-067310 A | 3/2003 |
| JP | 2004-219496 A | 8/2004 |
| WO | WO 91/19103 A1 | 12/1991 |
| WO | WO 92/03181 A1 | 3/1992 |
| WO | WO 94/05347 A1 | 3/1994 |
| WO | WO 94/09274 A1 | 4/1994 |
| WO | WO 94/13955 A1 | 6/1994 |
| WO | WO 95/00185 A1 | 1/1995 |
| WO | WO 97/15228 A1 | 5/1997 |
| WO | WO 97/37698 A1 | 10/1997 |
| WO | WO 98/41759 A1 | 9/1998 |
| WO | WO 98/46879 A1 | 10/1998 |
| WO | WO 99/01663 A1 | 1/1999 |
| WO | WO 99/12587 A1 | 3/1999 |
| WO | WO 99/37352 A1 | 7/1999 |
| WO | WO 99/44651 A1 | 9/1999 |
| WO | WO 99/53974 A2 | 10/1999 |
| WO | WO 00/06701 A1 | 2/2000 |
| WO | WO 00/12148 A2 | 3/2000 |
| WO | WO 00/35531 A1 | 6/2000 |
| WO | WO 00/38591 A2 | 7/2000 |
| WO | WO 00/41612 A2 | 7/2000 |
| WO | WO 00/64508 A1 | 11/2000 |
| WO | WO 01/02724 A1 | 1/2001 |
| WO | WO 01/24867 A1 | 4/2001 |
| WO | WO 01/83016 A3 | 11/2001 |
| WO | WO 02/070039 A2 | 9/2002 |
| WO | WO 03/006088 A1 | 1/2003 |
| WO | WO 03/048582 A1 | 6/2003 |
| WO | WO 03/103745 A2 | 12/2003 |
| WO | WO 2005/028000 A1 | 3/2005 |
| WO | WO 2006/051023 A1 | 5/2006 |

OTHER PUBLICATIONS

G.H. Jang, et al., "Stability Analysis of a Hydrodynamic Journal Bearing with Rotating Herringbone Grooves," *ASME Journal of*

(56) References Cited

OTHER PUBLICATIONS

*Tribology*, ASME/STLE Tribology Conference, Cancun, Mexico, Oct. 27-30, 2002, pp. 291-300.
"Fluid Dynamic Bearings (FDB): New Technology to Replace Ball Bearings in Western Digital Hard Drives," Western Digital, Jul. 2002.
International Bureau of WIPO, Search Report dated Feb. 14, 2005 for counterpart PCT Appl. No. PCT/US2004/029842.
IP Australia, Examiner's Report mailed Apr. 20, 2011 in Australian Patent Application No. 2007233078, 4 pages.
United States Patent and Trademark Office, Notice of Allowability mailed Mar. 23, 2011 in U.S. Appl. No. 12/565,651, 5 pages.
Japanese Patent Office, Second Office Action mailed Mar. 18, 2011 in Japanese Patent Application Serial No. 2006-526958, 16 pages.
IP Canadian Intellectual Property Office, Examiner's Report mailed Feb. 8, 2011 in Canadian Patent Application No. 2,579,637, 3 pages.
United States Patent and Trademark Office, Office Action mailed Jan. 25, 2011 in U.S. Appl. No. 11/950,328, 22 pages.
United States Patent and Trademark Office, Office Action mailed Jul. 23, 2010 in U.S. Appl. No. 11/950,328, 26 pages.
IP Singapore, Examiner's Report mailed Jun. 9, 2010 in Singapore Patent Application No. 200807202-7, 6 pages.
Japanese Patent Office, Office Action mailed May 19, 2010 in Japanese Patent Application Serial No. 2007-242976, 3 pages.
IP Canadian Intellectual Property Office, Examiner's Report mailed May 7, 2010 in Canadian Patent Application No. 2,579,637, 2 pages.
Japanese Patent Office, Office Action mailed Mar. 18, 2010 in Japanese Patent Application Serial No. 2006-526958, 5 pages.
WIPO, U.S. International Search Authority, International Search Report and Written Opinion mailed Jan. 7, 2010 in International Patent Application No. PCT/US09/55431, 14 pages.
IP Israel, Response to Office Action dated Jun. 6, 2009—Response filed Nov. 29, 2009 in Israeli Patent Application No. 174362, 3 pages.
United States Patent and Trademark Office, Notice of Allowance mailed Nov. 5, 2009 in U.S. Appl. No. 10/937,109, 6 pages.
United States Patent and Trademark Office, Office Action mailed Oct. 20, 2009 in U.S. Appl. No. 11/950,328, 16 pages.
IP Australia, Examiner's Report mailed Sep. 14, 2009 in Australian Patent Application No. 2004273831, 2 pages.
Chinese Patent Office, Office Action mailed Jun. 2, 2009 in Chinese Patent Application Serial No. 2004-80034041.7, 10 pages.
United States Patent and Trademark Office, Final Office Action mailed Apr. 16, 2009 in U.S. Appl. No. 10/937,109, 7 pages.
WIPO, U.S. International Search Authority, International Preliminary Report on Patentability mailed Feb. 24, 2009 in International Patent Application No. PCT/US2007/065717, 1 page.
United States Patent and Trademark Office, Notice of Allowance mailed Aug. 19, 2008 in U.S. Appl. No. 10/940,419, 5 pages.
United States Patent and Trademark Office, Office Action mailed Jul. 15, 2008 in U.S. Appl. No. 10/937,109, 6 pages.
United States Patent and Trademark Office, Notice of Allowance mailed Jul. 10, 2008 in U.S. Appl. No. 10/937,091, 6 pages.
WIPO, U.S. International Search Authority, International Search Report and Written Opinion mailed May 16, 2008 in International Patent Application No. PCT/US2007/065717, 9 pages.
United States Patent and Trademark Office, Office Action mailed Jan. 24, 2008 in U.S. Appl. No. 10/940,419, 13 pages.
United States Patent and Trademark Office, Office Action mailed Oct. 22, 2007 in U.S. Appl. No. 10/937,109, 12 pages.
United States Patent and Trademark Office, Office Action mailed Oct. 9, 2007 in U.S. Appl. No. 10/937,091, 11 pages.
IP Singapore, Examiner's Report mailed May 2, 2007 in Singapore Patent Application No. 200601784-2, 9 pages.
WIPO, U.S. International Search Authority, International Preliminary Report on Patentability mailed Mar. 21, 2006 in International Patent Application No. PCT/US04/29842, 1 page.
WIPO, U.S. International Search Authority, Written Opinion dated Jul. 18, 2005 in International Patent Application No. PCT/US2004/029357, 8 pages.
WIPO, U.S. International Search Authority, International Search Report dated Jul. 18, 2005 in International Application No. PCT/US2004/029357, 5 pages.
Schmitz-Rode et al., "An Expandable Percutaneous Catheter Pump for Left Ventricular Support," *Journal of the American College of Cardiology*, vol. 45, No. 11, Elsevier Inc., Jun. 7, 2005, 8 pages.
WIPO, U.S. International Search Authority, International Search Report mailed Feb. 14, 2005 in International Patent Application No. PCT/US04/29842, 1 page.
WIPO, U.S. International Search Authority, Written Opinion mailed Feb. 14, 2005 in International Patent Application No. PCT/US04/29842, 3 pages.
Western Digital, Fluid Dynamic bearings (FDB): New Technology to Replace Ball Bearings in Western Digital Hard Drives, Jul. 2002.
Taiwanese Patent Office, Official Letter mailed Nov. 19, 1999 in Taiwanese Patent Application Serial No. 093128212, 7 pages.
Schima et al., "An Implantable Seal-less Centrifugal pump with integrated double-disk motor," *Department of Cardiothoracic Surgery*, University of Vienna Austria, Jul. 19, 1995, pp. 639-43.
Jang, G.H. et al., "Stability Analysis of a Hydrodynamic Journal Bearing with Rotating Herringbone Grooves," *ASME Journal of Tribology*, ASME/ STLE Tribology Conference, Cancun, Mexico Oct. 27-30, 2002, Apr. 2003, vol. 125, pp. 291-300.
Jang, G.H. et al., "Nonlinear Dynamic Analysis of a Hydrodynamic Journal Bearing Considering the Effect of a Rotating or Stationary Herringbone Groove," *ASME Journal of Tribology*, STLE/ASME Tribology Conference, San Francisco, California Oct. 22-24, 2001, Apr. 2002, vol. 124, pp. 297-304.
Takagaki et al., "A Novel Miniature Ventricular Assist Device for Hemodynamic Support," *ASAIO Journal*, Jul., 2001, Abstract only.
Reitan et al., Hydrodynamic Properties of a New Percutaneous Intra-aortic Axial Flow Pump, *ASAIO Journal*, May 2000, Abstract only.
Sharony et al., "Cardiopulmonary Support and Physiology- The Intra-Aortic CAnnula Pump: A Novel Assist Device for the Acutely Failing Heart," *The Journal for Thoracic and Cardiovascular Surgery*, vol. 118/ No. 5, Nov. 1999, pp. 924-929.
Nishimura et al., "The enabler cannula pump: a novel circulatorey support system," *The International Journal of Artificial Organs*, vol. 22, No. 5, May 1999, pp. 317-323, Abstract only.
Verkerke et al., "Numerical Simulation of the Pulsating Catheter Pump: A Left Ventricular Assist Device," *Artificial Organs*, vol. 23/ No. 10 1999, pp. 924-931.
Yamane, T. et al., "Design of Centrifugal Blood Pump with Magnetic Suspension," *Artificial Organs*, 19, Mar. 1, 1996, pp. 625-30.
Verkerke et al., "The PUCA pump: A Left Ventricular Assist Device," *Artificial Organs*, 17(5); 365-68; May 1993, Abstract only.

* cited by examiner

ROTARY BLOOD PUMP

CROSS-REFERENCE TO RELATED APPLICATIONS

This application is a divisional of U.S. patent application Ser. No. 10/940,419 filed Sep. 14, 2004 now U.S. Pat. No. 7,431,688, which claims the benefit of U.S. Provisional Application No. 60/504,233 of Wampler et al. filed Sep. 18, 2003, both of which are incorporated herein by reference.

FIELD OF THE INVENTION

This invention relates to the field of rotary pumps. In particular, this invention is drawn to bearings for various rotor and impeller architectures.

BACKGROUND OF THE INVENTION

Typical rotary pumps utilize an impeller wherein the movement of the impeller is constrained in five degrees of freedom (two angular, three translational) by mechanical contact bearings. Some working fluids may be damaged by the mechanical contact bearings. Blood pumped through pumps with contact bearings can experience hemolysis, i.e., damage to blood cells. In general, a hydraulically efficient and power efficient pump that can handle delicate working fluids such as blood is desirable for some applications.

U.S. Pat. No. 6,234,772 B1 of Wampler, et al., ("Wampler") describes a centrifugal blood pump having a repulsive radial magnetic bearing and an axial hydrodynamic bearing. U.S. Pat. No. 6,250,880 B1 of Woodard, et al. ("Woodard") describes a centrifugal blood pump with an impeller supported exclusively by hydrodynamic forces.

Both blood pumps are based on an axial flux gap motor design. The pump impeller carries the motor drive magnets thus serving as a motor rotor. In both cases, the drive magnets are disposed within the blades of the impeller. Drive windings reside outside the pump chamber but within the pump housing that serves as the motor stator. Integration of the motor and pump enables the elimination of drive shafts and seals for the pumps. The pump/motors include a back iron to increase the magnetic flux for driving the impeller.

Both blood pumps suffer from hydraulic inefficiencies due at least in part to the large, unconventional blade geometry required for disposing the magnets within the impeller blades.

The natural attraction between the magnets carried by the impeller and the back iron creates significant axial forces that must be overcome in order for the pump to work efficiently. Hydrodynamic bearings can damage blood cells as a result of shear forces related to the load carried by the hydrodynamic bearings despite the lack of contact between the impeller and the pump housing. Thus exclusive reliance on hydrodynamic bearings may be harmful to the blood.

SUMMARY OF THE INVENTION

In view of limitations of known systems and methods, various "contactless" bearing mechanisms are provided for a rotary pump as alternatives to mechanical contact bearings. Various rotor and housing design features are provided to achieve magnetic or hydrodynamic bearings. These design features may be combined. The lack of mechanical contact bearings enables longer life pump operation and less damage to working fluids such as blood.

In one embodiment, the pump includes a magnetic thrust bearing. The pump includes a pump housing defining a pumping chamber. The pump housing has a spindle extending into the pumping chamber. A spindle magnet assembly comprising first and second magnets is disposed within the spindle. The first and second magnets of the spindle magnet assembly are arranged proximate each other with their respective magnetic vectors opposing each other. The pump includes a rotor having an impeller configured to rotate about the spindle. A rotor magnet assembly comprising first and second magnets is disposed within a non-bladed portion of the rotor. The first and second magnets of the rotor magnet assembly are arranged proximate each other with their respective magnetic vectors opposing each other. The relative orientations of the spindle and rotor magnet assemblies are selected so that the spindle and rotor magnet assemblies attract each other. The rotor may include a grooved bore. In various embodiments, a hydrodynamic bearing is included for radial or axial support or both.

BRIEF DESCRIPTION OF THE DRAWINGS

The present invention is illustrated by way of example and not limitation in the figures of the accompanying drawings, in which like references indicate similar elements and in which.

DETAILED DESCRIPTION

Figure 1:
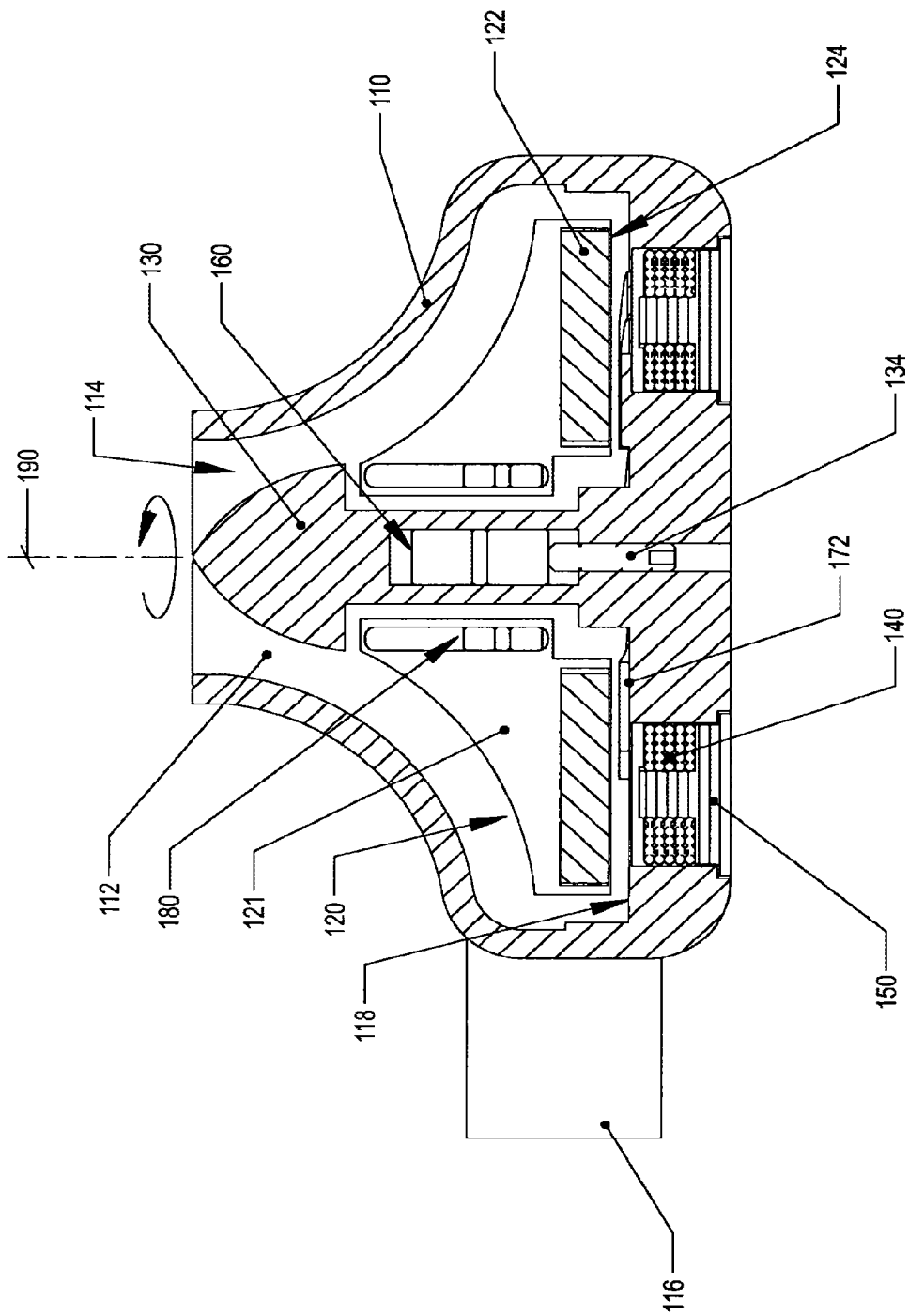
FIG. 1 illustrates a cross-section of a pump having a passive magnetic axial bearing.

FIG. 1 illustrates one embodiment of a centrifugal blood pump. The pump comprises a housing 110 defining a pumping chamber 112 between an inlet 114 and an outlet 116. Within the pumping chamber, a rotor 120 rotates about a spindle 130 protruding from a base of the pump housing. The rotor further comprises a bladed portion defining an impeller that provides the fluid moving surfaces. The impeller comprises one or more blades 121 that move fluids when the impeller rotates.

The terms "rotor" and "impeller" may be used interchangeably in some contexts. For example, when the rotor is rotating, the blade portion of the rotor is inherently rotating such that reference to rotation of either the impeller or the rotor is sufficient to describe both. When necessary, however, the term "non-bladed portion of the rotor" or "rotor excluding the impeller" may be used to specifically identify portions of the rotor other than the blades. Each blade of the rotor may separately be referred to as an impeller, however the term "impeller" is generally used to refer to a collective set of one or more blades.

The pump is based upon a moving magnet axial flux gap motor architecture. In one embodiment, the motor is a brushless DC motor. Drive magnets 122 carried by the rotor have magnetic vectors parallel to the rotor axis of rotation 190. In the illustrated embodiment, the drive magnets are disposed within a non-bladed portion of the rotor.

Drive windings 140 are located within the pump housing. Power is applied to the drive windings to generate the appropriate time-varying currents that interact with the drive magnets in order to cause the impeller to rotate. A back iron 150 enhances the magnetic flux produced by the motor rotor magnets. In one embodiment, either the face 124 of the bottom of the rotor or the opposing face 118 provided by the lower pump housing have surfaces (e.g., 172) contoured to produce a hydrodynamic bearing when the clearance between the rotor and the housing falls below a pre-determined threshold. In one embodiment, the pre-determined threshold is within a range of 0.0002 inches to 0.003 inches.

The natural attraction between the back iron 150 and the drive magnets 122 carried by the rotor can create a significant axial load on the rotor. This axial load is present in centrifugal pumps based on an axial flux gap motor architecture such as Wampler or Woodard. Woodard and Wampler both rely on hydrodynamic thrust bearings to overcome this axial loading force. Despite the lack of contact, hydrodynamic bearings can still damage blood cells as a result of shear forces related to the load carried by the hydrodynamic bearings.

The repulsive radial magnetic bearing of Wampler exacerbates the axial loads created by the magnetic attraction between the drive magnets and the back iron. Although the repulsive radial magnetic bearing creates radial stability, it introduces considerable axial instability. This axial instability can contribute further to the axial loading. This additional axial loading creates greater shear forces for any axial hydrodynamic bearing that can cause undesirable hemolysis for blood applications. In addition, the power required to sustain the hydrodynamic bearing increases as the load increases. Thus highly loaded hydrodynamic bearings can impose a significant power penalty.

The blood pump of FIG. 1 includes a magnetic axial bearing that serves to reduce or offset the axial load imposed on the rotor by the interaction between the drive magnets and the back iron. The axial magnetic bearing is formed by the interaction between a spindle magnet assembly 160 disposed within the spindle and a rotor magnet assembly 180 carried by the rotor. In the illustrated embodiment, the rotor magnet assembly 180 is disposed proximate the impeller, but the magnets of the rotor magnet assembly are not located within the blades. A set screw 134 permits longitudinal adjustment of the axial position of the axial magnetic bearing by moving the spindle magnet assembly along a longitudinal axis of the spindle.

Figure 2:
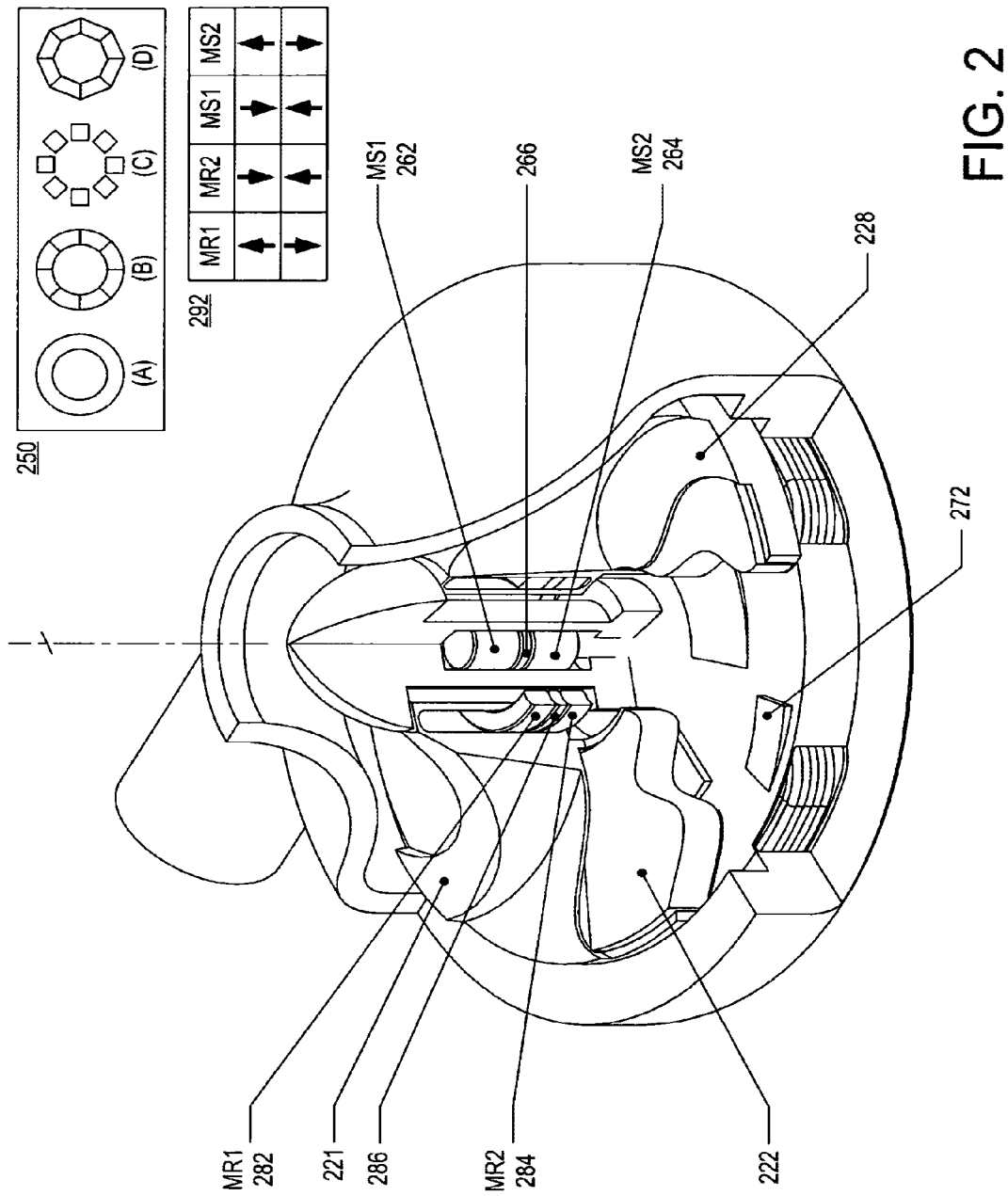
FIG. 2 illustrates one embodiment of the passive magnetic axial bearing.

FIG. 2 illustrates one embodiment of the axial magnetic bearing. The rotor magnet assembly includes a first rotor bearing magnet 282 and a second rotor bearing magnet 284 proximately disposed to each other. The first and second rotor bearing magnets are permanent magnets. In one embodiment, a pole piece 286 is disposed between them. A pole piece or flux concentrator serves to concentrate the magnetic flux produced by rotor bearing magnets 282 and 284. In an alternative embodiment, element 286 is merely a spacer to aid in positioning the first and second bearing magnets 282, 284 and does not serve to concentrate any magnetic flux. In other embodiments, element 286 is omitted so that the rotor magnet assembly does not include a spacer or a pole piece element.

In one embodiment, elements 282 and 284 are monolithic, ring-shaped permanent magnets. In alternative embodiments, the bearing magnets may be non-monolithic compositions. For example, a bearing magnet may be composed of a plurality of pie-shaped, arcuate segment-shaped, or other-shaped permanent magnet elements that collectively form a ring-shaped permanent magnet structure as shown in the chart 250 of FIG. 2.

The rotor axial bearing magnet assembly is distinct from the drive magnets 222 carried by a portion of the rotor other than the blades 221. In the illustrated embodiment, the drive magnets are disposed within the non-bladed portion 228 of the rotor.

The spindle magnet assembly includes a first spindle bearing magnet 262 and a second spindle bearing magnet 264. The first and second spindle bearing magnets are permanent magnets. In one embodiment, a pole piece 266 is disposed between them. Pole piece 266 concentrates the magnetic flux produced by the spindle bearing magnets 262 and 264. In an alternative embodiment, element 266 is merely a spacer for positioning the first and second spindle bearing magnets and does not serve to concentrate any magnetic flux. In other embodiments, element 266 is omitted so that the spindle magnet assembly does not include a spacer or a pole piece element.

In the illustrated embodiment, permanent magnets 262 and 264 are cylindrical. Other shapes may be utilized in alternative embodiments. The ring-shaped rotor magnets rotate with the impeller about a longitudinal axis of the spindle that is shared by the spindle bearing magnet assembly.

The permanent magnets of each of the spindle and rotor bearing assemblies are arranged such that the magnetic vectors of the individual magnets on either side of the intervening pole pieces oppose each other. Each side of a given pole piece is adjacent the same pole of different magnets. Thus the magnetic vectors of magnets 262 and 264 oppose each other (e.g., N-to-N or S-to-S). Similarly, the magnetic vectors of magnets 282 and 284 oppose each other.

The orientation of the magnets is chosen to establish an axial attraction whenever the bearings are axially misaligned. Note that the relative orientations of the spindle and rotor magnet assemblies are selected so that the spindle and rotor magnet assemblies attract each other (e.g., S-to-N, N-to-S). The magnet vector orientation selected for the magnets of one assembly determines the magnetic vector orientation for the magnets of the other assembly. Table 292 illustrates the acceptable magnetic vector combinations for the first and second rotor bearing magnets (MR1, MR2) and the first and second spindle bearing magnets (MS1, MS2). Forces such as the magnetic attraction between the back iron and drive magnets that tend to axially displace the magnet bearing assemblies are offset at least in part by the magnetic attraction between the axial bearings that provide an axial force to restore the axial position of the rotor.

FIG. 2 also illustrates wedges or tapered surfaces 272 that form a portion of a hydrodynamic bearing when the clearance between a face of the non-bladed portion of the rotor (see, e.g., bottom face 124 of FIG. 1) and the back of the pump housing falls below a pre-determined threshold. In various embodiments, this pre-determined threshold is within a range of 0.0002 inches to 0.003 inches. Thus in one embodiment, the pump includes an axial hydrodynamic bearing. The surface geometry providing the axial hydrodynamic bearing may be located on the rotor or the housing.

Although the spindle magnet assembly is intended to provide an axial magnetic bearing, the attractive force between the spindle and rotor magnet assemblies also has a radial component. This radial component may be utilized to offset radial loading of the impeller due to the pressure gradient across the impeller. The radial component also serves as a pre-load during initial rotation and a bias during normal operation to prevent eccentric rotation of the rotor about the spindle. Such an eccentric rotation can result in fluid whirl or whip which is detrimental to the pumping action. The biasing radial component helps to maintain or restore the radial position of the rotor and the pumping action, for example, when the pump is subjected to external forces as a result of movement or impact.

Instead of a spindle magnet assembly interacting with a rotor bearing magnet assembly to form the magnetic bearing, a ferromagnetic material might be used in lieu of one of a) the spindle magnet assembly, or b) the rotor bearing magnet assembly (but not both) in alternative embodiments.

The magnetic bearing is still composed of a spindle portion and a rotor portion, however, one of the spindle and the rotor portions utilizes ferromagnetic material while the other portion utilizes permanent magnets. The ferromagnetic material interacts with the magnets to create a magnetic attraction between the rotor and spindle. Examples of ferromagnetic materials includes iron, nickel, and cobalt.

In one embodiment, the ferromagnetic material is "soft iron". Soft iron is characterized in part by a very low coercivity. Thus irrespective of its remanence or retentivity, soft iron is readily magnetized (or re-magnetized) in the presence of an external magnetic field such as those provided by the permanent magnets of the magnetic bearing system.

Figure 3:
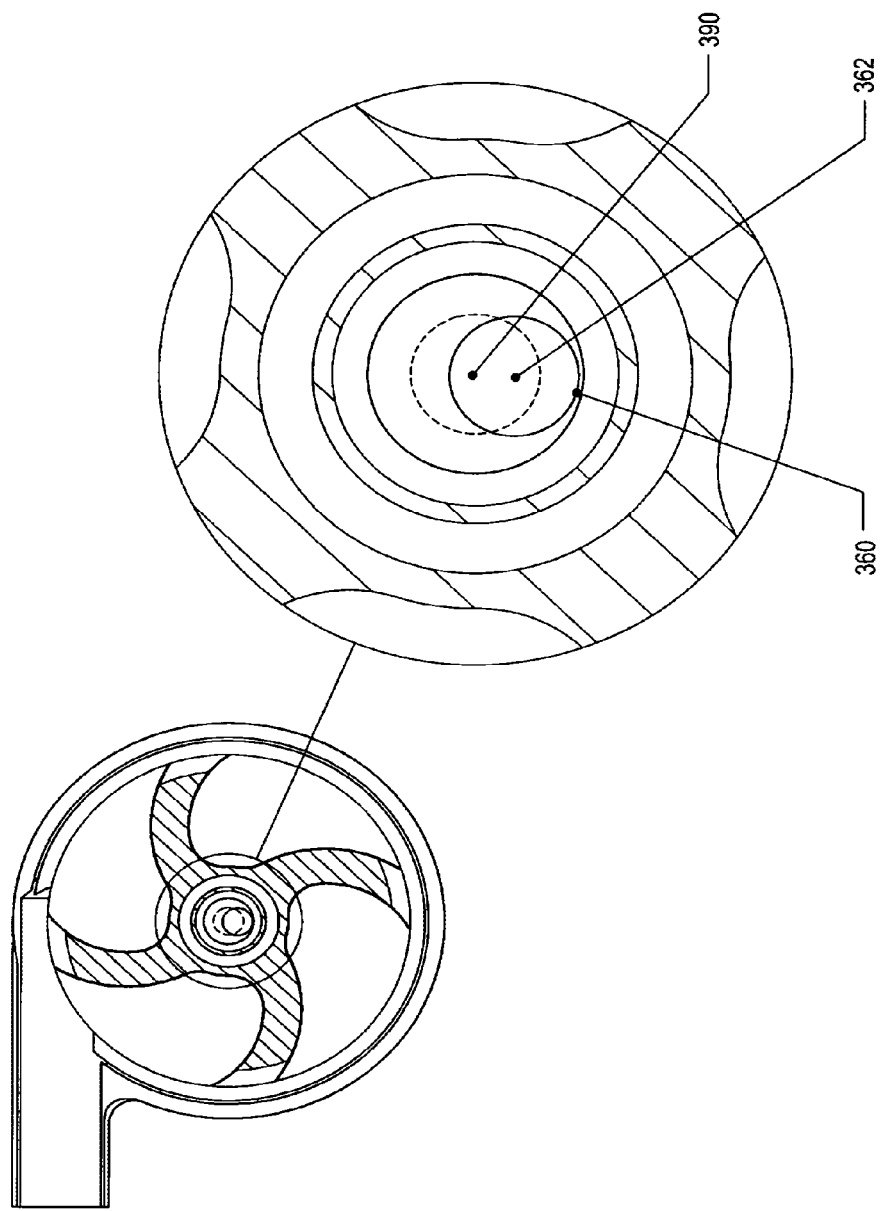
FIG. 3 illustrates center and off-center placement of the passive magnetic axial bearing.

FIG. 3 illustrates various locations for the placement of the spindle portion of the magnetic bearing. In one embodiment, the spindle magnet assembly 360 is axially aligned with a longitudinal axis 390 of the spindle so that the spindle and spindle magnet assembly share the same central longitudinal axis. In an alternative embodiment, the spindle magnet assembly is radially offset so that the spindle and spindle magnet assembly do not share the same central axis. In particular, the longitudinal axis 362 of the spindle magnet assembly 360 is displaced from the longitudinal axis 390 of the spindle. This latter positioning may be desirable to provide some radial biasing force. A difference in pressure across the impeller tends to push the impeller radially towards one side of the pump housing. This radial load may be offset at least in part by offsetting the spindle magnet assembly.

Although the spindle and rotor magnet assemblies are illustrated as comprising 2 magnetic elements each, the magnet assemblies may each comprise a single magnet instead. A greater spring rate may be achieved with multiple magnetic elements per assembly configured as illustrated instead of a single magnet per assembly. The use of two magnetic elements per assembly results in a bearing that tends to correct bi-directional axial displacements from a position of stability (i.e., displacements above and below the point of stability) with a greater spring rate than single magnetic elements per assembly.

The magnetic force generated by the axial magnetic bearing will exhibit a radial component in addition to their axial components. The radial component will tend to de-stabilize the impeller. In particular, the radial component may introduce radial position instability for the magnetic bearing of either FIG. 1 or 2.

This radial instability may be overcome using radial hydrodynamic bearings. Referring to FIG. 1, the pump may be designed for a radial hydrodynamic bearing (i.e., hydrodynamic journal bearing) located between the spindle 130 and the rotor along the bore of the rotor. The clearances illustrated in FIG. 1 are exaggerated. Hydrodynamic journal bearings require narrow clearances to be effective. In various embodiments, the hydrodynamic journal bearing clearances range from 0.0005-0.020 inches. The surface geometries suitable for axial (thrust) or radial (journal) hydrodynamic bearings may be located on either the rotor or on an associated portion of the housing (or spindle). In one embodiment, the surface geometry includes features such as one or more pads (i.e., a feature creating an abrupt change in clearance such as a step of uniform height). In alternative embodiments, the surface geometry includes features such as one or more tapers.

Figure 4:
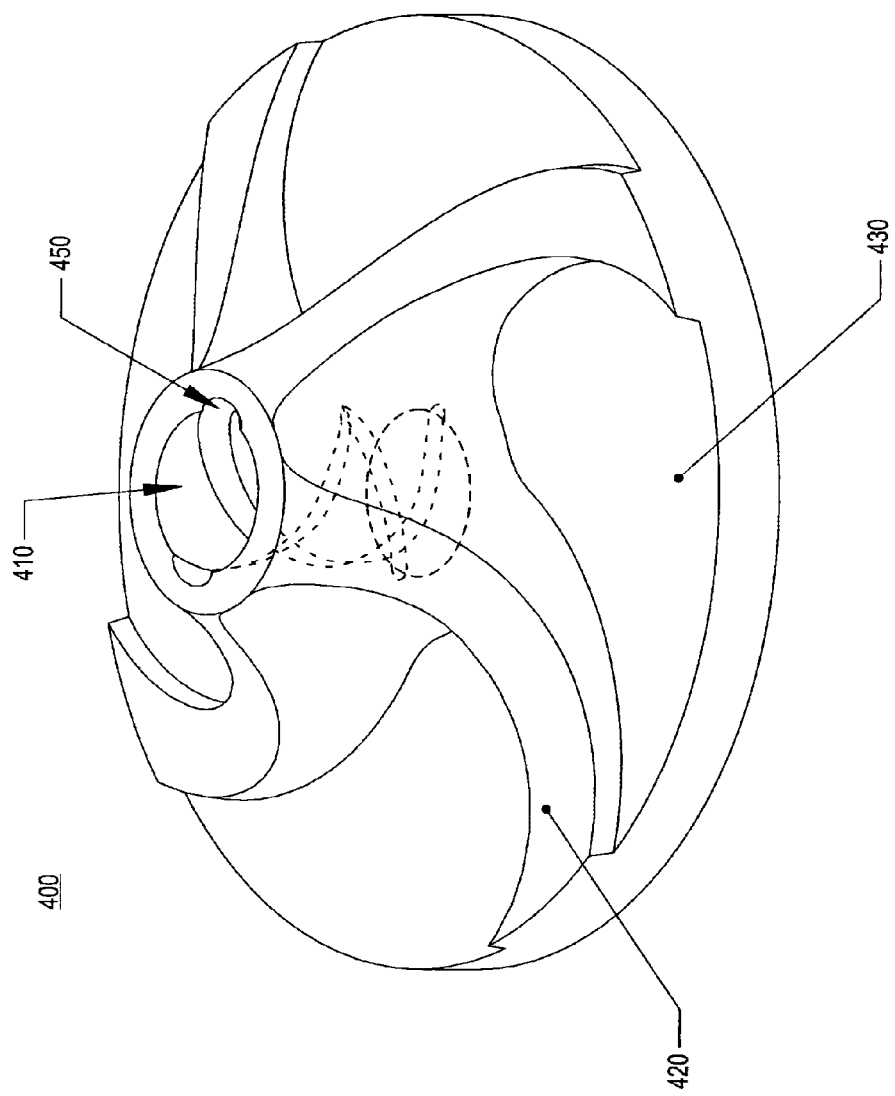
FIG. 4 illustrates one embodiment of an impeller.

FIG. 4 illustrates one embodiment of the rotor 400 including an impeller. The impeller includes a plurality of blades 420 used for pumping the working fluid such as blood. The rotor includes a bore 410. The rotor bore is coaxially aligned with the longitudinal axis of the spindle within the pump housing. Drive magnets (not illustrated) are disposed within the non-bladed portion 430 of the rotor (i.e., within the rotor but not within any blades of the impeller portion of the rotor). The motor rotor and pump impeller are thus integrated so that a drive shaft is not required. Elimination of the drive shaft also permits elimination of shaft seals for the pump.

In one embodiment, the rotor has a grooved bore. In particular, the bore has one or more helical grooves 450. The bore grooves have a non-zero axial pitch. The groove is in fluid communication with the working fluid of the pump during operation of the pump.

Figure 5:
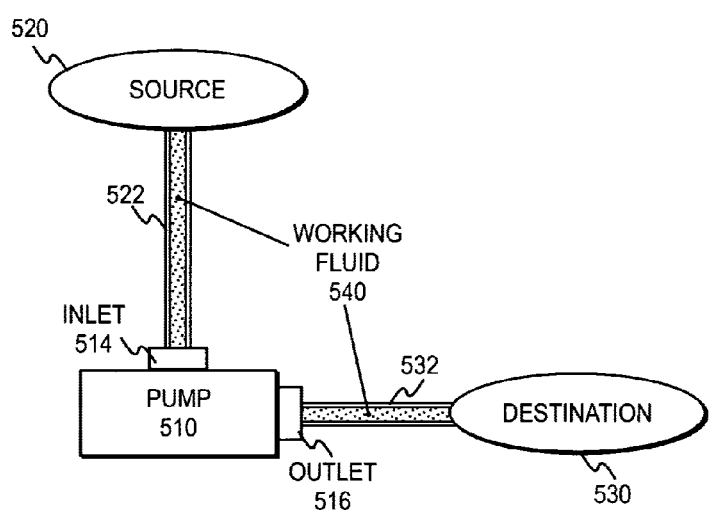
FIG. 5 illustrates one embodiment of the pump applied in a medical application.

FIG. 5 illustrates the pump 510 operationally coupled to move a working fluid 540 from a source 520 to a destination 530. A first working fluid conduit 522 couples the source to the pump inlet 514. A second working fluid conduit 532 couples the pump outlet 516 to the destination. The working fluid is the fluid moved by the pump from the source to the destination. In a medical application, for example, the working fluid might be blood. In one embodiment, the source and destination are arteries such that the pump moves blood from one artery to another artery.

Various "contactless" bearing mechanisms have been described as alternatives to mechanical contact bearings for rotary pumps. In particular, rotor, impeller, and housing design features are provided to achieve hydrodynamic or magnetic bearings. These design features may be used in conjunction with each other, if desired.

In the preceding detailed description, the invention is described with reference to specific exemplary embodiments thereof. Various modifications and changes may be made thereto without departing from the broader spirit and scope of the invention as set forth in the claims. The specification and drawings are, accordingly, to be regarded in an illustrative rather than a restrictive sense.

What is claimed is:

1. A pump apparatus comprising:
    a centrifugal pump housing defining a pumping chamber for pumping a liquid, the centrifugal pump housing having a spindle extending into the pumping chamber; and
    a spindle magnet assembly comprising a first and a second magnet disposed within the spindle, wherein the first and second magnets are arranged proximate each other with their respective magnetic vectors being parallel to an axis of rotation of a rotor of said pump;
    a rotor with a rotor magnet assembly comprising a third and a fourth magnet disposed within a non-bladed portion of the rotor, wherein the third and fourth magnets are arranged proximate each other with their respective magnetic vectors being parallel to said axis of rotation of said rotor,
    wherein said spindle and rotor magnet assemblies form a passive magnetic axial bearing wherein a relative orientation of the spindle and rotor magnet assemblies are selected so that the spindle and rotor magnet assemblies attract each other; and,
    a hydrodynamic bearing formed of a plurality of contoured surfaces between said housing and said rotor.

2. The pump apparatus of claim 1 wherein the first and second spindle magnets have one of a cylindrical and a ring-shaped form factor.

3. The apparatus of claim 1 wherein the spindle magnet assembly further comprises a pole piece disposed between the first and second magnets.

4. The apparatus of claim 1 wherein a longitudinal axis of the spindle magnet assembly is displaced from a longitudinal axis of the spindle.

5. The apparatus of claim 1 wherein the spindle supports a radial hydrodynamic bearing between the spindle and a bore of said rotor.

6. The apparatus of claim 1 wherein said rotor is configured to rotate about the spindle, the rotor including an impeller comprising at least one blade.

7. The apparatus of claim 6 wherein the rotor magnet assembly further comprises a pole piece disposed between the third and fourth magnets.

8. The apparatus of claim 6 wherein at least one of the third and fourth magnets has a ring-shaped form factor.

9. The apparatus of claim 6 wherein the third and fourth magnets are concentrically arranged about a bore of the rotor.

10. The apparatus of claim 6 wherein a bore of the rotor is grooved.

11. The apparatus of claim 6 further comprising: a plurality of drive magnets carried by a non-bladed portion of the rotor; and drive windings carried by the pump housing, wherein the drive magnets co-operate with the drive windings to rotate the rotor.

12. The apparatus according to claim 1, wherein said plurality of contoured surfaces include a plurality of discrete wedge-shaped surfaces.

13. The apparatus of claim 1 wherein said plurality of discrete wedge-shaped surfaces are disposed on said rotor.

14. The apparatus of claim 13, wherein said passive axial magnetic bearing is adjustable along an axis of said spindle.

15. The apparatus of claim 1, wherein said pump is a centrifugal pump for pumping a liquid.

16. A pump apparatus comprising:
a centrifugal pump housing defining a pumping chamber for pumping a liquid, the centrifugal pump housing having a spindle extending into the pumping chamber;
a rotor configured to rotate about the spindle, the rotor including an impeller comprising at least one blade;
a rotor portion of a magnetic bearing disposed within a non-bladed portion of the rotor; and
a spindle portion of the magnetic bearing disposed within the spindle,
wherein the spindle and rotor portions of the magnetic bearing constitute a passive magnetic axial bearing,
wherein at least one of the rotor and spindle portions of the magnetic bearing comprises a first and a second magnet, wherein the first and second magnets are arranged proximate each other with their respective magnetic vectors being parallel to said axis of rotation;
a plurality of contoured surfaces disposed between said pump housing and said rotor forming a hydrodynamic bearing.

17. The apparatus of claim 16 wherein the spindle portion of the magnetic bearing comprises first and second magnets arranged proximate each other with their respective magnetic vectors opposing each other, wherein the rotor portion of the magnetic bearing comprises first and second magnets arranged proximate each other with their respective magnetic vectors opposing each other.

18. The apparatus of claim 16 wherein the spindle portion of the magnetic bearing comprises first and second magnets arranged proximate each other with their respective magnetic vectors opposing each other, wherein the rotor portion of the magnetic bearing comprises ferromagnetic material.

19. The apparatus of claim 18 wherein the ferromagnetic material is soft iron.

20. The apparatus of claim 16 wherein the rotor portion of the magnetic bearing comprises first and second magnets arranged proximate each other with their respective magnetic vectors opposing each other, wherein the spindle portion of the magnetic bearing comprises ferromagnetic material.

21. The apparatus of claim 20 wherein the ferromagnetic material is soft iron.

22. The apparatus according to claim 16, wherein said plurality of contoured surfaces include a plurality of discrete wedge-shaped surfaces.

23. The apparatus of claim 22 wherein said plurality of discrete wedge-shaped surfaces are disposed on said rotor.

24. The apparatus of claim 16, wherein said passive axial magnetic bearing is adjustable along an axis of said spindle.

25. The apparatus of claim 16, wherein said pump is a centrifugal pump for pumping a liquid.

26. A pump apparatus comprising:
a centrifugal pump housing defining a pumping chamber for pumping a liquid, the pump housing having a spindle extending into the pumping chamber;
a rotor configured to rotate about the spindle on an axis of rotation, the rotor including an impeller comprising at least one blade;
a rotor portion of a magnetic bearing disposed within a non-bladed portion of the rotor;
a spindle portion of the magnetic bearing disposed within the spindle, wherein the spindle and rotor portions of the magnetic bearing constitute a passive magnetic axial bearing,
wherein at least one of the rotor and spindle portions of the magnetic bearing comprises a first and a second magnet, wherein the first and second magnets are arranged proximate each other with their respective magnetic vectors being parallel to said axis of rotation;
a plurality of contoured surfaces disposed between said housing and said rotor and forming a hydrodynamic bearing;
a plurality of drive magnets carried by a non-bladed portion of the rotor; and drive windings carried by the pump housing, wherein the drive magnets co-operate with the drive windings to rotate the rotor.

27. The apparatus of claim 26 wherein the spindle portion of the magnetic bearing comprises first and second magnets arranged proximate each other with their respective magnetic vectors opposing each other, wherein the rotor portion of the magnetic bearing comprises first and second magnets arranged proximate each other with their respective magnetic vectors opposing each other.

28. The apparatus of claim 26 wherein the spindle portion of the magnetic bearing comprises first and second magnets arranged proximate each other with their respective magnetic vectors opposing each other, wherein the rotor portion of the magnetic bearing comprises ferromagnetic material.

29. The apparatus of claim 28 wherein the ferromagnetic material is soft iron.

30. The apparatus of claim 26 wherein the rotor portion of the magnetic bearing comprises first and second magnets arranged proximate each other with their respective magnetic vectors opposing each other, wherein the spindle portion of the magnetic bearing comprises ferromagnetic material.

31. The apparatus of claim 30 wherein the ferromagnetic material is soft iron.

32. The apparatus of claim 26 wherein the rotor has a grooved bore.

33. The apparatus of claim 32 wherein the grooved bore comprises at least one groove following a helical path about the bore.

34. The apparatus of claim 32 wherein the grooved bore comprises a plurality of grooves.

35. The apparatus of claim 34 wherein each of the plurality of grooves follows a helical path about the bore.

36. The apparatus according to claim 26, wherein said plurality of contoured surfaces include a plurality of discrete wedge-shaped surfaces.

37. The apparatus of claim 36, wherein said plurality of discrete wedge-shaped surfaces are disposed on said rotor.

38. The apparatus of claim 26, wherein said passive axial magnetic bearing is adjustable along an axis of said spindle.

39. The apparatus of claim 26, wherein said pump is a centrifugal pump for pumping a liquid.

* * * * *